(12) United States Patent
Rothenberg

(10) Patent No.: US 7,794,407 B2
(45) Date of Patent: Sep. 14, 2010

(54) METHOD OF LOCATING THE TIP OF A CENTRAL VENOUS CATHETER

(75) Inventor: Peter M. Rothenberg, Laguna Niguel, CA (US)

(73) Assignee: Bard Access Systems, Inc., Salt Lake City, UT (US)

( * ) Notice: Subject to any disclaimer, the term of this patent is extended or adjusted under 35 U.S.C. 154(b) by 679 days.

(21) Appl. No.: 11/552,094

(22) Filed: Oct. 23, 2006

(65) Prior Publication Data

US 2008/0097232 A1  Apr. 24, 2008

(51) Int. Cl.
*A61B 5/02* (2006.01)
(52) U.S. Cl. ...................................................... 600/508
(58) Field of Classification Search .................. 600/508, 600/509, 510; 607/28, 122
See application file for complete search history.

(56) References Cited

U.S. PATENT DOCUMENTS

| | | | |
|---|---|---|---|
| 3,133,244 A | 5/1964 | Wojtulewicz | |
| 3,297,020 A | 1/1967 | Mathiesen | |
| 3,625,200 A | 12/1971 | Muller | |
| 3,674,014 A | 7/1972 | Tillander et al. | |
| 3,817,241 A * | 6/1974 | Grausz | 600/374 |
| 3,847,157 A | 11/1974 | Caillouette et al. | |
| 3,868,565 A | 2/1975 | Kuipers | |
| 3,995,623 A | 12/1976 | Blake et al. | |
| 4,063,561 A | 12/1977 | McKenna | |
| 4,072,146 A | 2/1978 | Howes | |
| 4,114,601 A | 9/1978 | Abels | |
| 4,149,535 A | 4/1979 | Volder et al. | |
| 4,173,228 A | 11/1979 | Steenwyk et al. | |
| 4,224,949 A | 9/1980 | Scott et al. | |
| 4,244,362 A | 1/1981 | Anderson | |

(Continued)

FOREIGN PATENT DOCUMENTS

AU  642647  11/1990

(Continued)

OTHER PUBLICATIONS

Arrow International, Inc., The Arrow-Johans RAECG Adapter-Making Proper Central Venous Catheter Placement More Reliabe (Model No. EG-04900), Technical Report 1987, USA.

(Continued)

*Primary Examiner*—George R Evanisko
*Assistant Examiner*—Hiba El-Kaissi
(74) *Attorney, Agent, or Firm*—Rutan & Tucker, LLP

(57) ABSTRACT

The invention includes a method of locating a tip of a central venous catheter ("CVC") having a distal and proximal pair of electrodes disposed within the superior vena cava, right atrium, and/or right ventricle. The method includes obtaining a distal and proximal electrical signal from the distal and proximal pair and using those signals to generate a distal and proximal P wave, respectively. A deflection value is determined for each of the P waves. A ratio of the deflection values is then used to determine a location of the tip of the CVC. Optionally, the CVC may include a reference pair of electrodes disposed within the superior vena cava from which a reference deflection value may be obtained. A ratio of one of the other deflection values to the reference deflection value may be used to determine the location of the tip of the CVC.

9 Claims, 7 Drawing Sheets

U.S. PATENT DOCUMENTS

| | | | |
|---|---|---|---|
| 4,317,078 A | 2/1982 | Weed et al. | |
| 4,327,722 A | 5/1982 | Groshong et al. | |
| 4,380,237 A | 4/1983 | Newbower | |
| 4,407,294 A | 10/1983 | Vilkomerson | |
| 4,429,693 A | 2/1984 | Blake et al. | |
| 4,431,005 A | 2/1984 | McCormick | |
| 4,431,214 A | 2/1984 | Buffington | |
| 4,445,501 A | 5/1984 | Bresler | |
| 4,469,106 A | 9/1984 | Harui | |
| 4,577,634 A * | 3/1986 | Gessman | 607/14 |
| 4,593,687 A | 6/1986 | Gray | |
| 4,595,012 A | 6/1986 | Webler et al. | |
| 4,601,706 A | 7/1986 | Aillon | |
| 4,622,644 A | 11/1986 | Hansen | |
| 4,652,820 A | 3/1987 | Maresca | |
| 4,667,230 A | 5/1987 | Arakawa et al. | |
| 4,674,518 A | 6/1987 | Salo | |
| 4,692,148 A | 9/1987 | Kantrowitz et al. | |
| 4,697,595 A | 10/1987 | Breyer et al. | |
| 4,700,997 A | 10/1987 | Strand | |
| 4,710,708 A | 12/1987 | Rorden et al. | |
| 4,737,794 A | 4/1988 | Jones | |
| 4,741,356 A | 5/1988 | Letzo et al. | |
| 4,742,356 A | 5/1988 | Kuipers | |
| 4,753,247 A | 6/1988 | Kirsner et al. | |
| 4,781,685 A | 11/1988 | Lehmann et al. | |
| 4,787,396 A | 11/1988 | Pidorenko | |
| 4,798,588 A | 1/1989 | Aillon | |
| 4,798,598 A | 1/1989 | Bonello et al. | |
| 4,813,729 A | 3/1989 | Speckhart | |
| 4,821,731 A | 4/1989 | Martinelli et al. | |
| 4,836,214 A | 6/1989 | Sramek | |
| 4,840,622 A | 6/1989 | Hardy | |
| 4,849,692 A | 7/1989 | Blood | |
| 4,852,580 A | 8/1989 | Wood | |
| 4,856,317 A | 8/1989 | Pidorenko et al. | |
| 4,901,725 A | 2/1990 | Nappholz et al. | |
| 4,905,698 A | 3/1990 | Strohl, Jr. et al. | |
| 4,911,174 A | 3/1990 | Pederson et al. | |
| 4,924,870 A | 5/1990 | Wlodarczyk et al. | |
| 4,945,305 A | 7/1990 | Blood | |
| 4,989,608 A | 2/1991 | Ratner | |
| 4,998,916 A | 3/1991 | Hammerslag et al. | |
| 5,005,592 A | 4/1991 | Cartmell | |
| 5,016,173 A | 5/1991 | Kenet et al. | |
| 5,029,585 A | 7/1991 | Lieber et al. | |
| 5,042,486 A | 8/1991 | Pfeiler et al. | |
| 5,045,071 A | 9/1991 | McCormick et al. | |
| 5,050,607 A | 9/1991 | Bradley et al. | |
| 5,057,095 A | 10/1991 | Fabian | |
| 5,076,278 A | 12/1991 | Vilkomerson et al. | |
| 5,078,140 A | 1/1992 | Kwoh | |
| 5,078,678 A * | 1/1992 | Katims | 604/28 |
| 5,078,714 A | 1/1992 | Katims | |
| 5,099,845 A | 3/1992 | Besz et al. | |
| 5,100,387 A | 3/1992 | Ng | |
| 5,105,829 A | 4/1992 | Fabian et al. | |
| 5,114,401 A | 5/1992 | Stuart et al. | |
| 5,121,750 A * | 6/1992 | Katims | 600/547 |
| 5,158,086 A | 10/1992 | Brown et al. | |
| 5,161,536 A | 11/1992 | Vilkomerson et al. | |
| 5,190,045 A | 3/1993 | Frazin | |
| 5,211,165 A | 5/1993 | Dumoulin et al. | |
| 5,211,636 A | 5/1993 | Mische | |
| 5,214,615 A | 5/1993 | Bauer et al. | |
| 5,220,924 A | 6/1993 | Frazin | |
| 5,240,004 A | 8/1993 | Walinsky et al. | |
| 5,247,171 A | 9/1993 | Wlodarczyk et al. | |
| 5,255,680 A | 10/1993 | Darrow et al. | |
| 5,257,636 A | 11/1993 | White | |
| 5,257,979 A | 11/1993 | Jagpal | |
| 5,267,569 A | 12/1993 | Lienhard | |
| 5,270,810 A | 12/1993 | Nishimura | |
| 5,273,042 A | 12/1993 | Lynch et al. | |
| 5,275,053 A | 1/1994 | Wlodarczyk et al. | |
| 5,280,786 A | 1/1994 | Wlodarczyk et al. | |
| 5,307,072 A | 4/1994 | Jones, Jr. | |
| 5,313,949 A | 5/1994 | Yock | |
| 5,318,025 A | 6/1994 | Dumoulin et al. | |
| 5,337,678 A | 8/1994 | Grout et al. | |
| 5,341,807 A | 8/1994 | Nardella | |
| 5,343,865 A | 9/1994 | Gardineer et al. | |
| 5,375,596 A | 12/1994 | Twiss et al. | |
| 5,376,083 A | 12/1994 | Mische | |
| 5,385,053 A | 1/1995 | Wlodarczyk et al. | |
| 5,398,683 A | 3/1995 | Edwards et al. | |
| 5,411,485 A | 5/1995 | Tennican et al. | |
| 5,413,107 A | 5/1995 | Oakley et al. | |
| 5,422,478 A | 6/1995 | Wlodarczyk et al. | |
| 5,425,367 A | 6/1995 | Shapiro et al. | |
| 5,425,370 A | 6/1995 | Vilkomerson | |
| 5,425,382 A | 6/1995 | Golden et al. | |
| 5,427,114 A | 6/1995 | Colliver et al. | |
| 5,429,132 A | 7/1995 | Guy et al. | |
| 5,429,617 A | 7/1995 | Hammersmark et al. | |
| 5,433,729 A | 7/1995 | Adams et al. | |
| 5,437,276 A | 8/1995 | Takada et al. | |
| 5,437,277 A | 8/1995 | Dumoulin et al. | |
| 5,438,873 A | 8/1995 | Wlodarczyk et al. | |
| 5,443,066 A | 8/1995 | Dumoulin et al. | |
| 5,445,150 A | 8/1995 | Dumoulin et al. | |
| 5,450,846 A | 9/1995 | Goldreyer | |
| 5,456,256 A | 10/1995 | Schneider et al. | |
| 5,464,016 A | 11/1995 | Nicholas et al. | |
| 5,476,090 A | 12/1995 | Kishi et al. | |
| 5,487,729 A | 1/1996 | Avellanet et al. | |
| 5,492,538 A | 2/1996 | Johlin, Jr. | |
| 5,500,012 A | 3/1996 | Brucker et al. | |
| 5,513,637 A | 5/1996 | Twiss et al. | |
| 5,515,853 A | 5/1996 | Smith et al. | |
| 5,540,230 A | 7/1996 | Vilkomerson | |
| 5,542,938 A | 8/1996 | Avellanet et al. | |
| 5,588,442 A | 12/1996 | Scovil et al. | |
| 5,592,939 A | 1/1997 | Martinelli | |
| 5,598,846 A | 2/1997 | Peszynski et al. | |
| 5,599,299 A | 2/1997 | Weaver et al. | |
| 5,600,330 A | 2/1997 | Blood | |
| 5,622,169 A | 4/1997 | Golden et al. | |
| 5,622,170 A | 4/1997 | Schulz | |
| 5,645,065 A | 7/1997 | Shapiro et al. | |
| 5,651,047 A | 7/1997 | Moorman et al. | |
| 5,666,958 A | 9/1997 | Rothenberg et al. | |
| 5,669,383 A | 9/1997 | Johnson | |
| 5,669,388 A | 9/1997 | Vilkomerson | |
| 5,676,673 A | 10/1997 | Ferre et al. | |
| 5,695,479 A | 12/1997 | Jagpal | |
| 5,713,362 A | 2/1998 | Vilkomerson | |
| 5,715,817 A | 2/1998 | Stevens-Wright et al. | |
| 5,716,389 A | 2/1998 | Walinsky et al. | |
| 5,722,412 A | 3/1998 | Pflugrath et al. | |
| 5,727,552 A | 3/1998 | Ryan | |
| 5,727,553 A | 3/1998 | Saad | |
| 5,729,129 A | 3/1998 | Acker | |
| 5,731,996 A | 3/1998 | Gilbert | |
| 5,740,808 A * | 4/1998 | Panescu et al. | 600/424 |
| 5,742,394 A | 4/1998 | Hansen | |
| 5,744,953 A | 4/1998 | Hansen | |
| 5,749,835 A | 5/1998 | Glantz | |
| 5,749,938 A | 5/1998 | Coombs | |
| 5,752,513 A | 5/1998 | Acker et al. | |
| 5,762,064 A | 6/1998 | Polvani | |
| 5,767,669 A | 6/1998 | Hansen et al. | |
| 5,767,960 A | 6/1998 | Orman et al. | |
| 5,769,786 A | 6/1998 | Wiegel | |

| | | | |
|---|---|---|---|
| 5,769,843 A | 6/1998 | Abela et al. | |
| 5,769,881 A | 6/1998 | Schroeppel et al. | |
| 5,775,322 A | 7/1998 | Silverstein et al. | |
| 5,775,332 A | 7/1998 | Goldman | |
| 5,779,638 A | 7/1998 | Vesely et al. | |
| 5,792,055 A | 8/1998 | McKinnon et al. | |
| 5,795,298 A | 8/1998 | Vesely et al. | |
| 5,797,849 A | 8/1998 | Vesely et al. | |
| 5,800,497 A | 9/1998 | Bakels et al. | |
| 5,803,089 A | 9/1998 | Ferre et al. | |
| 5,817,022 A | 10/1998 | Vesely | |
| 5,824,031 A | 10/1998 | Cookston et al. | |
| 5,829,444 A | 11/1998 | Ferre et al. | |
| 5,831,260 A | 11/1998 | Hansen | |
| 5,833,608 A | 11/1998 | Acker | |
| 5,836,990 A | 11/1998 | Li | |
| 5,840,024 A | 11/1998 | Taniguchi et al. | |
| 5,840,031 A | 11/1998 | Crowley | |
| 5,842,986 A | 12/1998 | Avrin et al. | |
| 5,843,076 A | 12/1998 | Webster, Jr. et al. | |
| 5,843,153 A | 12/1998 | Johnston et al. | |
| 5,846,198 A | 12/1998 | Killmann | |
| 5,868,673 A | 2/1999 | Vesely | |
| 5,879,297 A | 3/1999 | Haynor et al. | |
| 5,893,363 A | 4/1999 | Little et al. | |
| 5,899,860 A | 5/1999 | Pfeiffer et al. | |
| 5,902,238 A | 5/1999 | Golden et al. | |
| 5,913,820 A | 6/1999 | Bladen et al. | |
| 5,931,818 A | 8/1999 | Werp et al. | |
| 5,941,858 A | 8/1999 | Johnson | |
| 5,944,023 A | 8/1999 | Johnson et al. | |
| 5,953,683 A | 9/1999 | Hansen et al. | |
| 5,967,978 A | 10/1999 | Littmann et al. | |
| 5,967,991 A | 10/1999 | Gardineer et al. | |
| 5,978,705 A * | 11/1999 | KenKnight et al. ............ 607/5 |
| 5,984,908 A | 11/1999 | Davis et al. | |
| 5,997,473 A | 12/1999 | Taniguchi et al. | |
| 6,011,988 A | 1/2000 | Lynch et al. | |
| 6,014,473 A | 1/2000 | Hossack et al. | |
| 6,014,580 A | 1/2000 | Blume et al. | |
| 6,019,724 A | 2/2000 | Gronningsaeter et al. | |
| 6,019,725 A | 2/2000 | Vesely et al. | |
| 6,032,070 A | 2/2000 | Flock et al. | |
| 6,052,610 A | 4/2000 | Koch | |
| 6,059,718 A | 5/2000 | Taniguchi et al. | |
| 6,073,043 A | 6/2000 | Schneider | |
| 6,076,007 A | 6/2000 | England et al. | |
| 6,082,366 A | 7/2000 | Andra et al. | |
| 6,099,524 A | 8/2000 | Lipson et al. | |
| 6,102,044 A | 8/2000 | Naidyhorski | |
| 6,112,111 A | 8/2000 | Glantz | |
| 6,129,668 A | 10/2000 | Haynor et al. | |
| 6,135,961 A | 10/2000 | Pflugrath et al. | |
| 6,138,681 A | 10/2000 | Chen et al. | |
| 6,139,496 A | 10/2000 | Chen et al. | |
| 6,144,300 A | 11/2000 | Dames et al. | |
| 6,172,499 B1 | 1/2001 | Ashe | |
| 6,173,199 B1 | 1/2001 | Gabriel | |
| 6,173,715 B1 | 1/2001 | Sinanan et al. | |
| 6,176,829 B1 | 1/2001 | Vilkomerson | |
| 6,193,743 B1 | 2/2001 | Brayton et al. | |
| 6,200,305 B1 | 3/2001 | Berthiaume et al. | |
| 6,208,884 B1 | 3/2001 | Kumar et al. | |
| 6,216,028 B1 | 4/2001 | Haynor et al. | |
| 6,223,087 B1 | 4/2001 | Williams | |
| 6,226,547 B1 | 5/2001 | Lockhart et al. | |
| 6,230,046 B1 | 5/2001 | Crane et al. | |
| 6,238,344 B1 | 5/2001 | Gamelsky et al. | |
| 6,241,673 B1 | 6/2001 | Williams et al. | |
| 6,246,231 B1 | 6/2001 | Ashe | |
| 6,246,898 B1 | 6/2001 | Vesely et al. | |
| 6,248,072 B1 | 6/2001 | Murkin et al. | |
| 6,253,770 B1 | 7/2001 | Acker et al. | |
| 6,263,230 B1 | 7/2001 | Haynor et al. |
| 6,266,563 B1 | 7/2001 | KenKnight et al. |
| 6,272,374 B1 | 8/2001 | Flock et al. |
| 6,292,678 B1 | 9/2001 | Hall et al. |
| 6,293,955 B1 | 9/2001 | Houser et al. |
| 6,323,769 B1 | 11/2001 | Dames et al. |
| 6,323,770 B1 | 11/2001 | Dames et al. |
| 6,324,416 B1 | 11/2001 | Seibert |
| 6,325,540 B1 | 12/2001 | Lounsberry et al. |
| 6,329,916 B1 | 12/2001 | Dames et al. |
| 6,332,874 B1 | 12/2001 | Eliasen et al. |
| 6,346,081 B1 | 2/2002 | Vilkomerson |
| 6,350,160 B1 | 2/2002 | Feuersanger et al. |
| 6,368,285 B1 | 4/2002 | Osadchy et al. |
| 6,373,388 B1 | 4/2002 | Dames et al. |
| 6,374,670 B1 | 4/2002 | Spelman et al. |
| 6,377,857 B1 | 4/2002 | Brayton et al. |
| 6,385,472 B1 | 5/2002 | Hall et al. |
| 6,406,442 B1 | 6/2002 | McFann et al. |
| 6,417,839 B1 | 7/2002 | Odell |
| 6,418,332 B1 | 7/2002 | Mastrototaro et al. |
| 6,418,335 B2 | 7/2002 | Avrin et al. |
| 6,423,002 B1 | 7/2002 | Hossack |
| 6,423,050 B1 | 7/2002 | Twardowski |
| 6,427,079 B1 | 7/2002 | Schneider et al. |
| 6,442,416 B1 | 8/2002 | Schultz |
| 6,473,167 B1 | 10/2002 | Odell |
| 6,474,341 B1 | 11/2002 | Hunter et al. |
| 6,477,402 B1 | 11/2002 | Lynch et al. |
| 6,484,118 B1 | 11/2002 | Govari et al. |
| 6,493,573 B1 | 12/2002 | Martinelli et al. |
| 6,496,715 B1 | 12/2002 | Lee et al. |
| 6,505,062 B1 | 1/2003 | Ritter et al. |
| 6,508,802 B1 | 1/2003 | Rosengart et al. |
| 6,515,657 B1 | 2/2003 | Zanelli |
| 6,516,212 B1 | 2/2003 | Bladen et al. |
| 6,516,807 B1 | 2/2003 | Panescu et al. |
| 6,522,907 B1 | 2/2003 | Bladen et al. |
| 6,524,303 B1 | 2/2003 | Garibaldi |
| 6,528,991 B2 | 3/2003 | Ashe |
| 6,540,699 B1 | 4/2003 | Smith et al. |
| 6,542,766 B2 | 4/2003 | Hall et al. |
| 6,546,270 B1 | 4/2003 | Goldin et al. |
| 6,556,858 B1 | 4/2003 | Zeman |
| 6,574,518 B1 | 6/2003 | Lousberry et al. |
| 6,575,908 B2 | 6/2003 | Barnes et al. |
| 6,593,884 B1 | 7/2003 | Gilboa et al. |
| 6,610,058 B2 | 8/2003 | Flores |
| 6,618,612 B1 | 9/2003 | Acker et al. |
| 6,645,148 B2 | 11/2003 | Nguyen-Dinh et al. |
| 6,648,875 B2 | 11/2003 | Simpson et al. |
| 6,652,506 B2 | 11/2003 | Bowe et al. |
| 6,672,308 B1 | 1/2004 | Gaspari et al. |
| 6,685,644 B2 | 2/2004 | Seo et al. |
| 6,689,119 B1 | 2/2004 | Di Caprio et al. |
| 6,690,963 B2 | 2/2004 | Ben-Haim et al. |
| 6,701,918 B2 | 3/2004 | Fariss et al. |
| 6,711,429 B1 | 3/2004 | Gilboa et al. |
| 6,719,724 B1 | 4/2004 | Walker et al. |
| 6,743,177 B2 | 6/2004 | Ito et al. |
| 6,754,596 B2 | 6/2004 | Ashe |
| 6,755,789 B2 | 6/2004 | Stringer et al. |
| 6,772,001 B2 | 8/2004 | Maschke et al. |
| 6,774,624 B2 | 8/2004 | Anderson et al. |
| 6,783,536 B2 | 8/2004 | Vilsmeier et al. |
| 6,784,660 B2 | 8/2004 | Ashe |
| 6,785,571 B2 | 8/2004 | Glossop et al. |
| 6,788,967 B2 | 9/2004 | Ben-Haim et al. |
| 6,815,651 B2 | 11/2004 | Odell |
| 6,817,364 B2 | 11/2004 | Garibaldi et al. |
| 6,834,201 B2 | 12/2004 | Gillies et al. |
| 6,856,823 B2 | 2/2005 | Ashe |
| 6,862,467 B2 | 3/2005 | Moore et al. |

| | | |
|---|---|---|
| 6,879,160 B2 | 4/2005 | Jakab |
| 6,889,091 B2 | 5/2005 | Hine et al. |
| 6,936,010 B2 | 8/2005 | Fang et al. |
| 6,947,788 B2 | 9/2005 | Gilboa et al. |
| 6,950,689 B1 | 9/2005 | Willis et al. |
| 6,976,987 B2 | 12/2005 | Flores |
| 6,980,843 B2 | 12/2005 | Eng et al. |
| 6,980,921 B2 | 12/2005 | Anderson et al. |
| 6,999,821 B2 | 2/2006 | Jenney et al. |
| 7,026,927 B2 | 4/2006 | Wright et al. |
| 7,027,634 B2 | 4/2006 | Odell |
| 7,066,914 B2 | 6/2006 | Andersen |
| 7,096,148 B2 | 8/2006 | Anderson et al. |
| 7,096,870 B2 | 8/2006 | Lamprich et al. |
| 7,104,980 B1 | 9/2006 | Laherty et al. |
| 7,106,431 B2 | 9/2006 | Odell |
| 7,107,105 B2 | 9/2006 | Bjorklund et al. |
| 7,148,970 B2 | 12/2006 | de Boer |
| 7,214,191 B2 | 5/2007 | Stringer et al. |
| 7,231,243 B2 | 6/2007 | Tearney et al. |
| 7,270,662 B2 | 9/2007 | Visram et al. |
| 7,310,150 B2 | 12/2007 | Guillermo et al. |
| 7,321,228 B2 | 1/2008 | Govari |
| 7,355,716 B2 | 4/2008 | de Boer et al. |
| 7,366,376 B2 | 4/2008 | Shishkov et al. |
| 7,366,562 B2 | 4/2008 | Dukesherer et al. |
| 7,382,949 B2 | 6/2008 | Bouma et al. |
| 7,418,169 B2 | 8/2008 | Tearney et al. |
| 7,447,408 B2 | 11/2008 | Bouma et al. |
| 7,452,358 B2 | 11/2008 | Stern et al. |
| 7,538,859 B2 | 5/2009 | Tearney et al. |
| 7,551,293 B2 | 6/2009 | Yelin et al. |
| 7,640,053 B2 | 12/2009 | Verin |
| 2002/0022777 A1 | 2/2002 | Crieghton et al. |
| 2002/0032391 A1 | 3/2002 | McFann et al. |
| 2002/0165448 A1 | 11/2002 | Ben-Haim et al. |
| 2002/0165534 A1 | 11/2002 | Hayzelden et al. |
| 2003/0011359 A1 | 1/2003 | Ashe |
| 2003/0013966 A1 | 1/2003 | Barnes et al. |
| 2003/0040671 A1 | 2/2003 | Somogyi et al. |
| 2003/0083698 A1* | 5/2003 | Whitehurst et al. ............ 607/3 |
| 2003/0100849 A1 | 5/2003 | Jang |
| 2003/0152290 A1 | 8/2003 | Odell |
| 2003/0160721 A1 | 8/2003 | Gilboa et al. |
| 2003/0173953 A1 | 9/2003 | Ashe |
| 2003/0216639 A1 | 11/2003 | Gilboa et al. |
| 2003/0220557 A1 | 11/2003 | Cleary et al. |
| 2003/0233042 A1 | 12/2003 | Ashe |
| 2004/0024301 A1 | 2/2004 | Hockett et al. |
| 2004/0082916 A1 | 4/2004 | Jenkins |
| 2004/0087877 A1 | 5/2004 | Besz et al. |
| 2004/0088136 A1 | 5/2004 | Ashe |
| 2004/0097803 A1 | 5/2004 | Panescu |
| 2004/0133130 A1 | 7/2004 | Ferry et al. |
| 2004/0135069 A1 | 7/2004 | Odell |
| 2004/0138570 A1 | 7/2004 | Nita et al. |
| 2004/0230271 A1 | 11/2004 | Wang et al. |
| 2004/0260174 A1 | 12/2004 | Keene |
| 2005/0004450 A1 | 1/2005 | Ben-Haim et al. |
| 2005/0033150 A1 | 2/2005 | Takahashi et al. |
| 2005/0038355 A1 | 2/2005 | Gellman et al. |
| 2005/0049486 A1 | 3/2005 | Urquhart et al. |
| 2005/0075561 A1 | 4/2005 | Golden |
| 2005/0085716 A1 | 4/2005 | Hamm et al. |
| 2005/0105081 A1 | 5/2005 | Odell |
| 2005/0105101 A1 | 5/2005 | Duling et al. |
| 2005/0165301 A1 | 7/2005 | Smith et al. |
| 2005/0203368 A1 | 9/2005 | Verin |
| 2005/0205081 A1 | 9/2005 | Barker et al. |
| 2005/0215945 A1 | 9/2005 | Harris et al. |
| 2005/0222532 A1 | 10/2005 | Bertolero et al. |
| 2006/0015003 A1 | 1/2006 | Moaddes et al. |
| 2006/0025677 A1 | 2/2006 | Verard et al. |
| 2006/0116571 A1 | 6/2006 | Maschke et al. |
| 2006/0173407 A1 | 8/2006 | Shaughnessy et al. |
| 2007/0016068 A1 | 1/2007 | Grunwald et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0049846 A1 | 3/2007 | Bown et al. |
| 2007/0232882 A1 | 10/2007 | Glossop et al. |
| 2008/0082136 A1* | 4/2008 | Gaudiani ...................... 607/9 |
| 2008/0097232 A1 | 4/2008 | Rothenberg |
| 2008/0146940 A1 | 6/2008 | Jenkins et al. |
| 2008/0154100 A1 | 6/2008 | Thalmeier et al. |
| 2009/0005675 A1 | 1/2009 | Grunwald et al. |
| 2009/0101577 A1 | 4/2009 | Fulkerson et al. |
| 2009/0118612 A1 | 5/2009 | Grunwald et al. |
| 2009/0227952 A1 | 9/2009 | Blakstvedt et al. |

FOREIGN PATENT DOCUMENTS

| | | |
|---|---|---|
| AU | 5586590 | 11/1990 |
| AU | 2001283703 | 5/2002 |
| AU | 2006202149 | 6/2006 |
| AU | 2006904933 | 9/2006 |
| CA | 2420676 | 2/2002 |
| EP | 0359697 | 3/1990 |
| EP | 0362821 | 4/1990 |
| EP | 0399536 | 11/1990 |
| EP | 1311226 A1 | 8/2008 |
| FR | 2545349 | 11/1984 |
| JP | 01097440 A | 4/1989 |
| JP | 03173542 | 7/1991 |
| JP | 4090741 U | 8/1992 |
| JP | 4505748 (T) | 10/1992 |
| JP | 10043310 A | 2/1998 |
| JP | 11128237 | 5/1999 |
| JP | 2001161683 | 6/2001 |
| JP | 2001340334 A | 12/2001 |
| JP | 2003299654 | 10/2003 |
| JP | 2003334191 A | 11/2003 |
| JP | 2002520893 | 2/2004 |
| JP | 2004505748 | 2/2004 |
| WO | WO-9002514 A1 | 3/1990 |
| WO | WO-9203090 | 3/1992 |
| WO | WO-9404938 | 3/1994 |
| WO | WO-9641119 | 12/1996 |
| WO | WO-0019906 | 4/2000 |
| WO | WO-0040155 | 7/2000 |
| WO | WO-0215973 | 2/2002 |
| WO | WO-02094102 A1 | 11/2002 |
| WO | WO-03061752 | 7/2003 |
| WO | WO-2005033524 A1 | 4/2005 |
| WO | WO-2005033574 A1 | 4/2005 |
| WO | WO-2006031765 A2 | 3/2006 |
| WO | WO-2006031765 A3 | 3/2006 |
| WO | WO-2006/074509 A1 | 7/2006 |
| WO | WO-2006074510 A1 | 7/2006 |
| WO | WO-2006074510 A1 | 7/2006 |
| WO | WO-2006078677 A2 | 7/2006 |
| WO | WO-2006078677 A2 | 7/2006 |
| WO | WO-2008028253 | 3/2008 |
| WO | WO-2008/083111 A1 | 7/2008 |
| WO | WO-2009070836 | 6/2009 |
| WO | WO-2009100158 A1 | 8/2009 |

OTHER PUBLICATIONS

B. Braun, Certofix central venous catheter for placement using the Seldinger Technique with simultaneous ECG lead option.

C.R. Bard, Inc., Bard Electrophysiology Product Catalogue, Bard catheters, pp. 74-75 (2002), USA.

"ASCENSION to Launch New 3D Guidance™ Tracker at TCT 2006." Press Releases from Ascension website: www.ascension-tech.com/news/press_101106.php.

Andropoulos, et al. "A Controlled Study of the Transesophageal Echocardiography to Guide Central Venous Catheter Placement in Congetital Heart Surgery Patients." The International Anesthesia Research Society, vol. 89, pp. 65-70, 1999.

Aslamy, et al. "MRI of Central Venous Anatomy: Implications for Central Venous Catheter Insertion." American College of Chest Physicians, Jun. 8, 2009.

AURORA® System Technical Specifications.

B.Braun Website, "The Optimal Position of the Central Venous Catheter." http://www.cvcpartner.com/index.cfm18F1BDEA1310466194960A39F4E90968 (2009).

Cavatorta, et al., "Central Venous Catheter Placement in Hemodialysis: Evaluation of Electrocardiography Using a Guidewire." The Journal of Vascular Access, vol. 2, pp. 45-50, 2001.

Chaturvedi et al., "Catheter Malplacement During Central Venous Cannulation Through Arm Veins in Pediatric Patients." Journal of Neurosurgical Anesthesiology, vol. 15, No. 3 pp. 170-175, Jan. 2003.

Chu, et al., "Accurate Central Venous Port-A Catheter Placement: Intravenous Electrocardiography and Surface Landmark Techniques Compared by Using Transesophageal Echocardiography." The International Anesthesia Research Society, vol. 98, pp. 910-914, 2004.

Clifford, et al. "Assessment of Hepatic Motion Secondary to Respiration for Computer Assisted Interventions." Computer Aided Surgery, vol. 7, pp. 291-299, 2002.

Corsten, et al., "Central Placement Catheter Placement Using the ECG-Guided Cavafix-Certodyn SD Catheter." Journal of Clinical Anesthesiology, vol. 6, Nov./Dec. 1994.

David, et al., "Is ECG-Guidance a Helpful Method to Correctly Position a Central Venous Catheter During Prehospital Emergency Care?" Acta Anaesthesiologica Scandinavica, vol. 49, pp. 1010-1014, 2005.

DELTEC Cath-Finder® Tracking System Operation Manual, 1994.

Gebhard, et al., "The accuracy of Electrocardiogram-Controlled Central Line Placement." The International Anesthesia Research Society, vol. 104, No. 1 Jan. 2007.

Gonzales, et al. "Peripherally Inserted Central Catheter Placement in Swine Using Magnet Detection." Journal of Intravenous Nursing, vol. 22, No. 3, May/Jun. 1999.

Hoffmann, et al. "New Procedure in Transesophageal Echocardiography: Multiplane Transesophageal Echocardiography and Transesophageal Stress Echocardiography." Herz, vol. 18, No. 5, pp. 269-277, Oct. 1993.

Madan, et al. "Right Atrial Electrocardiography: A Technique for the Placement of Central Venous Catheters for Chemotherapy or Intravenous Nutrition." British Journal of Surgery, vol. B1, pp. 1604-1605, 1994.

McGee et al., "Accurate Placement of Central Venous Catheters: A Prospective, Randomize, Multicenter Trail." Critical Care Medicine, vol. 21 No. 8, Aug. 1993.

MICROBIRD™ Miniaturized DC Magnetic Sensors for Intra-body Navigation and Localization, Specifications, 2005.

MICRONIX CathRite™ Cardiac Access Device Brochure.

NEUROMETER® CPT, Clinical Applications. Neurotron , Inc. wesbite: www.neurotron.com/CLINAPS.html.

NEUROMETER® CPT, Frequently Asked Questions. Neurotron , Inc. wesbite: www.neurotron.com/CPTFAQ/html.

NEUROMETER® CPT, Products Page. Neurotron , Inc. wesbite: www.neurotron.com/products.html.

NEUROMETER® Electrodiagnostic Neuroselective Sensory Nerve Evaluation: Charts, Tables, Documents & Downloads. Neurotron , Inc. wesbite: www.neurotron.com/downloads.html.

Pawlik, et al., "Central Venous Catheter Placement: Comparison of the Intravascular Guidewire and the Fluid col. Electrocardiograms." European Journal of Anaesthesiology, vol. 41, pp. 594-599, 2004.

Pittiruti, et al. "The EKG Method for Positioning the Tip of PICCs: Results from Two Preliminary Studies." Java, vol. 13, No. 4, pp. 179-185, 2008.

Sacolick, et al. "Electromagnetically Tracked Placement of a Peripherally Inserted Central Catheter." SPIE Medical Imaging, 2004 Proceedings.

Salem, et al. "A New Peripherally Implanted Subcutaneous Permanent Central Venous Access Device for Patients Requiring Chemotherapy." Journal of Clinical Oncology, vol. 11, No. 11 , pp. 2181-2185, Nov. 1993.

Schafer et al. "Incorrect placement of a vena cava catheter and its prevention by intra-atrial ECG." Anaesthesist. Jan. 1988;37(1):49-51.

Schummer, et al. "Central Venous Catheters—The inability of 'intra-atrial Ecg' to prove adequate positioning." British Journal of Anaesthesia, vol. 93, No. 2, pp. 193-198, 2004.

Simon, et al., "Central Venous Catheter Placement in Children: Evaluation of Electrocardiography Using J-Wire." Paediatric Anaesthesia vol. 9, pp. 501-504, 1999.

Starkhammar et al. "Cath-Finder Catheter Tracking System: A New Device for Positioning of Central Venous Catheters. Early Experience from Implantation of Brachial portal Systems." Acta Anaesthesiol Scandinavia, vol. 34, No. 4 pp. 296-300.

STEREROTAXIS Magetic Navigation System with Navigant™ User Interface, 2005 Brochure.

TRAXAL Technologies, Tracking Technology website overview: www.traxal.com/rd/rd_classroom_trackingtechnology.htm.

VIASYS Health Care Inc. Cortrak© Fact Sheet.

VIASYS MedSystems, Cortrak© Systems Brochure.

Watters, et al. "Use of Electrocardiogram to Position Right Atrial Catheters During Surgery." Annals of Surgery, vol. 225, No. 2, pp. 165-171, 1997.

Worley, Seth J. "Use of a Real-Time Three-Dimensional Magenetic Navigation System for Radiofrequency Ablation of Accessory Pathways." PACE, vol. 21 pp. 1636-1643, Aug. 1998.

Zaaroor, et al. "Novel Magnetic Technology for Intraoperative Intracranial Frameless Navigation: In Vivo and in Vitro Results." Neurosurgery, vol. 48, No. 5. pp. 1100-1107, May 2001.

March 13, 2009 International Search Report for international application No. PCT/US2009/033116 filed Feb. 4, 2009.

* cited by examiner

METHOD OF LOCATING THE TIP OF A CENTRAL VENOUS CATHETER

BACKGROUND OF THE INVENTION

1. Field of the Invention

The present invention is directed generally to devices for and methods of locating a catheter inside a body and more particularly to devices for and methods of locating the tip of a central venous catheter inside the superior vena cava, right atrium, and/or right ventricle using information obtained from an electrocardiogram.

2. Description of the Related Art

Central venous catheters ("CVC") include any catheter designed to utilize the central veins (e.g., subclavian and superior vena cava) or right sided cardiac chambers for the delivery and/or withdrawal of blood, blood products, therapeutic agents, and/or diagnostic agents. CVCs also include catheters inserted into the central veins or right sided cardiac chambers for the acquisition of hemodynamic data. Standard central venous catheters for intravenous access, dialysis catheters, percutaneously introduced central catheters ("PICC" lines), and right heart ("Swan-Ganz™") catheters are examples of CVCs.

The standard of care for placing a CVC dictates that the tip of the CVC lie just above and not inside the right atrium. In fact, in 1989, the Food and Drug Administration issued a warning citing an increased risk of perforation of the right atrium, clot formation, and arrhythmias among other potential complications resulting from the tip of the CVC being placed inside the right atrium.

While CVCs have been used for many years, determining the position of the tip of the CVC has always been problematic. Currently, a chest x-ray is used to determine the position of the tip of the CVC. Because CVC may be a radiopaque and/or include radiopaque materials, the CVC is visible on an x-ray. However, this method has several drawbacks. For example, obtaining a chest x-ray is labor intensive and expensive. In recent years, CVCs, which were traditionally placed in a hospital in-patient setting, are being placed in an outpatient setting more frequently. In an outpatient setting, obtaining a chest x-ray to determine the position of the tip of the CVC can be very cumbersome and may not be obtained in a timely manner. Therefore, using a chest x-ray to determine the position of the tip of the CVC may introduce a considerable delay, prolonging the procedure. Generally, the operator will leave the patient to perform other duties while the x-ray is processed. If the tip is improperly placed, the operator must return to the patient's bedside to reposition the CVC. To reposition the CVC, the operator must open the sterile dressing, cut the sutures, re-suture, and redress the wound, all of which potentially expose the patient to discomfort and infection.

In addition to the need to know where the tip is during initial placement, the CVC may migrate or otherwise move after the initial placement and require re-positioning. Therefore, the operator must monitor or periodically reevaluate the location of the tip.

An electrocardiogram (ECG) measures electrical potential changes occurring in the heart. Referring to FIGS. 1A-1C, the ECG measurements may be visualized or displayed as an ECG trace, which includes ECG waveforms. The P wave portion of the ECG waveforms represents atrial muscle depolarization: the first half is attributable to the right atrium and the second half to the left atrium. Under normal circumstances, atrial muscle depolarization is initiated by a release of an excitatory signal from the sino-atrial node, a specialized strip of tissue located at the juncture of the superior vena cava ("SVC") and right atrium.

Techniques of using ECG waveforms to locate the tip of a CVC have been available since the 1940's. Some of these prior art devices construct an intravascular ECG trace by placing an electrode near the tip of the CVC and using that electrode to measure the voltage near the tip of the CVC relative to a surface electrode(s) and/or a second electrode spaced from the first.

These techniques have shown that both the magnitude and shape of the P wave change depending upon the positioning or location of the electrode attached to the tip of the CVC. Referring to FIGS. 1A and 1B, two exemplary ECG traces are provided for illustrative purposes.

FIG. 1A is an ECG trace made when the electrode attached to tip of the CVC is in the SVC. This tip location corresponds to position "1" depicted in FIG. 2A. The portion of the ECG trace corresponding to an exemplary P wave produced when the electrode attached to the tip is located in position "1" is labeled "P1."

FIG. 1B is an ECG trace made when the electrode attached to the tip of the CVC is approaching the sino-atrial node and stops at a location adjacent to the sino-atrial node. These tip locations correspond to moving the tip from a position "2" to position "3" depicted in FIG. 2A. The portion of the ECG trace corresponding to an exemplary P wave produced when the electrode attached to the tip is approaching the sino-atrial node is labeled "P2" and the portion of the ECG trace corresponding to an exemplary P wave produced when the electrode attached to the tip is located adjacent to the sino-atrial node is labeled "P3."

Normally as the electrode attached to the tip of the CVC moves from the SVC (position "1") toward the sino-atrial node (position "3"), the maximum value of the absolute value of the voltage of the P wave increases dramatically. When the electrode attached to tip of the CVC is adjacent to the sino-atrial node (position "3"), the voltage of the P wave (please see "P3" of FIG. 1B) reaches a maximum value that is more than twice the value experienced in the SVC and may be as large as eight times the voltage in the SVC. When this occurs, the tip of the CVC is considered to have entered into the right atrium. Because the magnitude of the P wave more than doubles when the electrode attached to tip of the CVC is adjacent to the sino-atrial node, this information may be used to place the tip of the CVC within 1-2 cm proximal to the sino-atrial node. Additionally, as the electrode attached to tip of the CVC moves from the SVC toward the right atrium, the shape of the P wave changes from a "u" shape (FIG. 1A) to a spike-like shape (FIG. 1B).

Referring to FIG. 2B, another exemplary illustration of the P wave portion of the ECG trace produced when the electrode attached to the tip of the CVC is located at positions 1-5 depicted in FIG. 2A is provided. The P wave portions of the ECG traces of FIG. 2B are labeled with the letter "P" and occur between the vertical dashed lines. Each of the exemplary traces is numbered to correspond to positions "1" through "5." Therefore, the ECG trace "1" was produced when the electrode attached to the tip was located in the SVC. The trace "2" was produced when the electrode attached to the tip was in position "2." And, the trace "3" was produced when the electrode attached to the tip was adjacent to the sino-atrial node.

As the electrode attached to tip of the CVC is advanced further into the right atrium, the polarity of the P wave "P" changes from predominantly negative near the top of the right atrium (position "3") to isoelectric (i.e., half has a positive polarity and half has a negative polarity) near the middle of the right atrium (position "4") to almost entirely positive at the bottom of the right atrium (position "5"). These changes in the P wave "P" are illustrated in traces "3" through "5."

FIG. 1C is an ECG trace made when the electrode attached to tip of the CVC is in the right ventricle. The portion of the ECG trace corresponding to an exemplary P wave produced when the electrode attached to the tip is labeled "P6." When the electrode attached to tip of the CVC is advanced into the right ventricle, the maximum magnitude of the absolute value of the P wave "P6" approximates the maximum magnitude of the absolute value of the P wave "P1" when the electrode attached to tip of the CVC was inside the SVC above the sino-atrial node (i.e., located at position "1"). However, the polarity of the first half of P wave "P6," which corresponds to the right atrium, is opposite.

The first technique developed for viewing the ECG waveform during the insertion of a CVC used a column of saline disposed within a hollow tube or lumen longitudinally traversing the CVC. The column of saline provides a conductive medium. Saline was inserted into the lumen by a saline filled syringe with a metal needle. The needle of the syringe remained within the entrance to the lumen or port in contact with the column of saline after the lumen was filled. One end of a double-sided alligator clip was attached to the needle and the other end was attached to an ECG lead, which in turn was attached to an ECG monitor. By using the saline solution filled CVC as a unipolar electrode and a second virtual electrode generated by ECG software from three surface electrodes, an intravascular ECG was obtained. The operator would adjust the position of the tip of the CVC based on the magnitude and shape of the P wave displayed by the ECG monitor.

Subsequently, this technique was modified by substituting an Arrow-Johans adapter for the metal needle. The Arrow-Johans adapter is a standard tubing connector with a embedded conductive ECG eyelet. The Arrow-Johans adapter may be placed in line with any conventional CVC. In a closed system, the tubing and CVC may be filled with saline, i.e., a conductive medium, and the CVC used as a unipolar electrode in conjunction with surface electrodes and a standard ECG monitor. The ECG eyelet is placed in contact with the saline in the lumen of the CVC. One end of the ECG lead is attached to the ECG eyelet and the other end to the ECG monitor for displaying the intravascular ECG waveforms. Because the system must be closed to prevent the saline from leaking out, this system works best after the guide wire used to thread the CVC forward has been withdrawn, i.e., after placement has been completed. Therefore, although the catheter may be withdrawn after initial placement, it may not be advanced into proper position.

BBraun introduced its Certofix catheter to be used in conjunction with its Certodyne adapter. In this system, a patch lead with two ends has an alligator clip connected to one end. The alligator clip is clipped to the CVC guide wire. The other end of the patch lead includes a connector that is plugged into the Certodyne adapter. The ECG may be obtained during placement and the catheter may be advanced or withdrawn as desired. However, the Certodyne adapter has many moving parts and is not sterile, making the procedure cumbersome to perform and the operative field more congested. Additionally, the sterile field may become contaminated by the non-sterile equipment.

With respect to all of these prior art methods of using an ECG trace to place the tip of the CVC, some degree of expertise is required to interpret the P waves measured because the user must advance the guide wire slowly and watch for changes in the P wave. If the catheter is inserted too far too quickly and the changes to the P wave go unnoticed (i.e., the operator fails to notice the increase or spike in the voltage experienced when the electrode attached to the tip is in the right atrium), the operator may mistakenly believe the tip is in the SVC when, in fact, the tip is in the right ventricle. If this occurs, advancing the tip may injure the patient.

U.S. Pat. Nos. 5,078,678 and 5,121,750 both issued to Katims teach a method of using the P wave portion of an ECG trace to guide placement of the tip of the CVC. The CVC includes two empty lumens into which a transmission line is fed or an electrolyte is added. Each of the lumens has a distal exit aperture located near the tip of the CVC. The two exit apertures are spaced from one another. In this manner, two spaced apart electrodes or a single anode/cathode pair are constructed near the tip of the CVC. The voltage or potential of one of the electrodes relative to the other varies depending upon the placement of the electrodes. The voltage of the electrodes is conducted to a catheter monitoring system. The catheter monitoring system detects increases and decreases in the voltage of the P wave. The voltage increases as the electrodes approach the sino-atrial node and decrease as the electrodes move away from the sino-atrial node. Based on whether the voltage is increasing or decreasing, the operator is instructed by messages on a screen to advance or withdraw the CVC.

While Katims teaches a method of locating the tip of a CVC relative to the sino-atrial node, Katims relies on advancing or withdrawing the CVC and observing the changes of the P wave. Katims does not disclose a method of determining the location of the tip of the CVC based on a single stationary position. Unless the entire insertion procedure is monitored carefully, the method cannot determine the position of the tip of the CVC. Further, the Katims method may be unsuitable for determining the location of a previously positioned stationary tip.

Other devices such as Bard's Zucker, Myler, Gorlin, and CVP/Pacing Lumen Electrode Catheters are designed primarily to pace. These devices include a pair of electrodes at their tip that are permanently installed and designed to contact the endocardial lining. These devices include a lumen, which may be used to deliver and/or withdraw medications or fluids as well as for pressure monitoring. These leads are not designed for tip location and do not include multi-lumen capability.

A method of obtaining an intravascular ECG for the purposes of placing a temporary pacing wire was described in U.S. Pat. No. 5,666,958 issued to Rothenberg et. al. Rothenberg et. al discloses a bipolar pacing wire having a distal electrode. The distal electrode serves as a unipolar electrode when the pacing wire is inserted into the chambers of the heart. The pacing wire is connected to a bedside monitor through a specialized connector for the purposes of displaying the ECG waveforms detected by the distal electrode.

Given the volume of CVCs placed yearly and the increasing demand particularly for PICC lines (devices that permit the delivery of intravenous therapeutic agents in the outpatient setting, avoiding the need for hospitalization) a great need exists for methods and devices related to locating the tip of a CVC. Particularly, devices and methods are needed that are capable of determining the location of the tip before the operator leaves the bedside of the patient. Further, a method of determining the location (SVC, right atrium, or right ventricle) of the tip from a single data point rather than from a series of data points collected as the catheter is moved may be advantageous. Such a system may be helpful during initial placement and/or repositioning. A need also exists for a device for or a method of interpreting the ECG waveforms that does not require specialized expertise. Methods and devices that avoid the need for hospital and x-ray facilities are also desirable. A need also exists for devices and methods related to determining the position of the tip of the CVC that are less expensive, expose patients to fewer risks, and/or are less cumbersome than the x-ray method currently in use.

BRIEF DESCRIPTION OF THE SEVERAL VIEWS OF THE DRAWING(S)

Figure 1A:
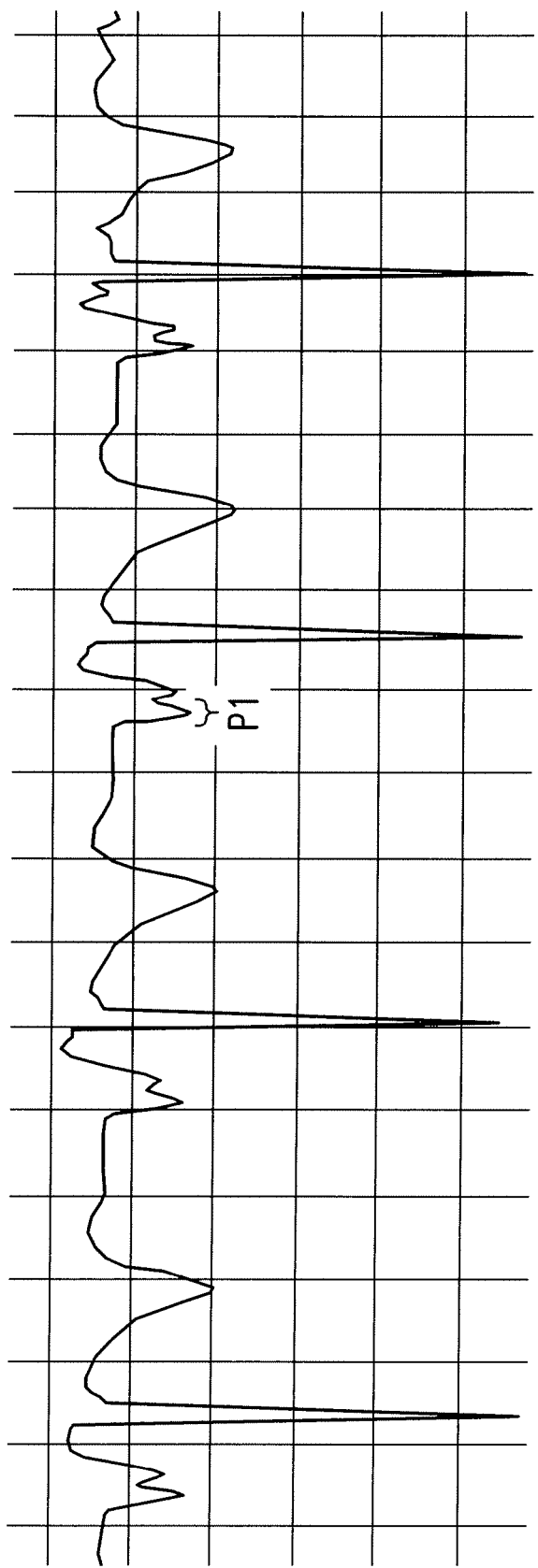
FIG. 1A is an exemplary ECG trace obtained from an electrode placed inside the SVC.
Figure 1B:
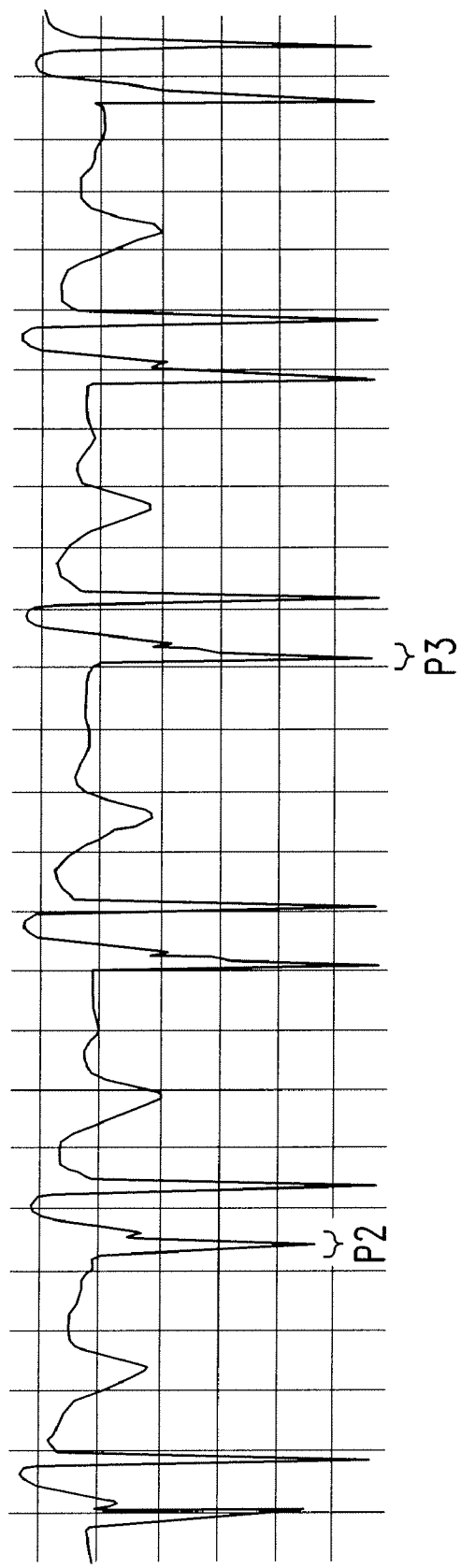
FIG. 1B is an exemplary ECG trace obtained from an electrode approaching the sino-atrial node and stopping adjacent thereto.
Figure 1C:
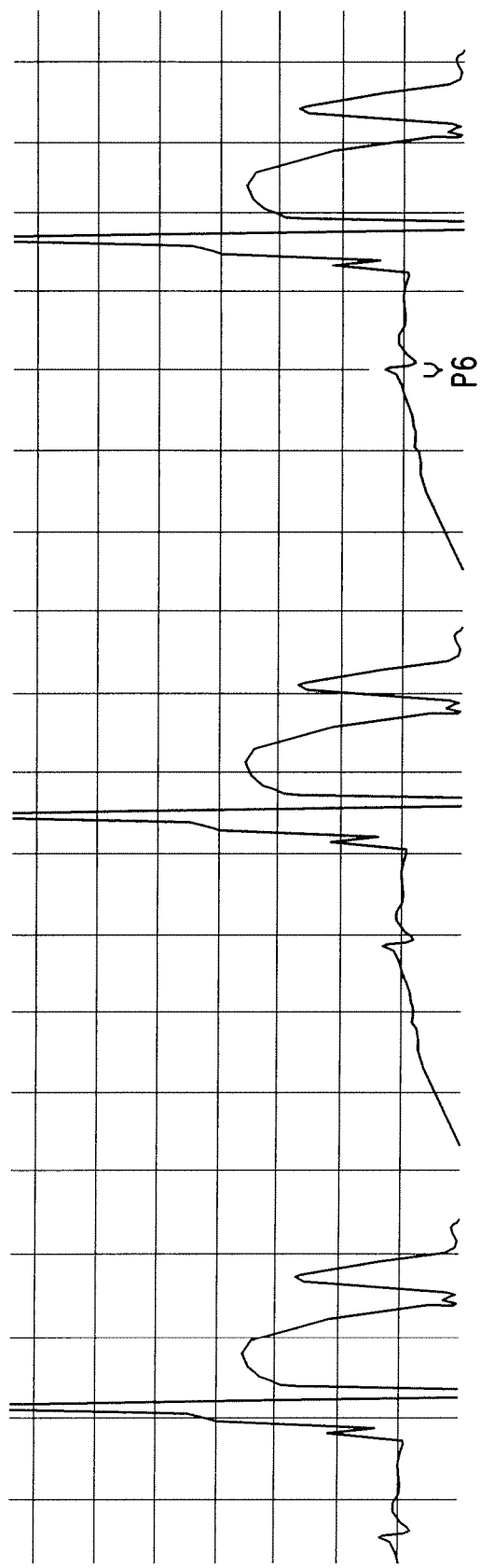
FIG. 1C is an exemplary ECG trace obtained from an electrode placed inside the right ventricle.
Figure 2B:
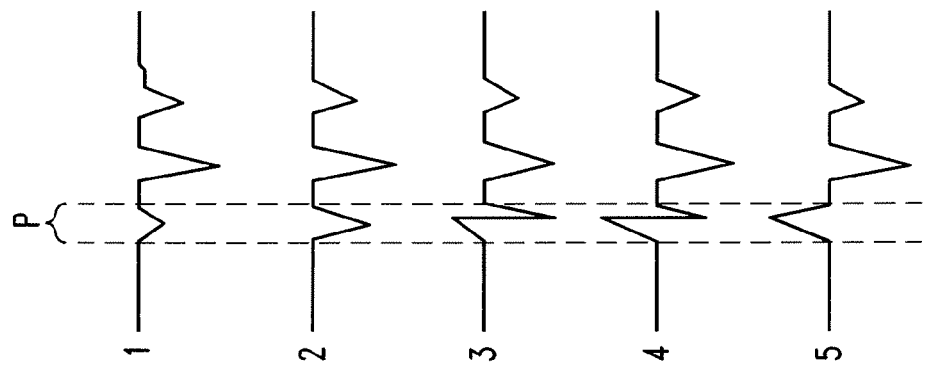
FIG. 2A is an illustration of a partial cross-section of the heart providing three exemplary tip locations 1, 2, 3, 4, and 5.
Figure 2A:
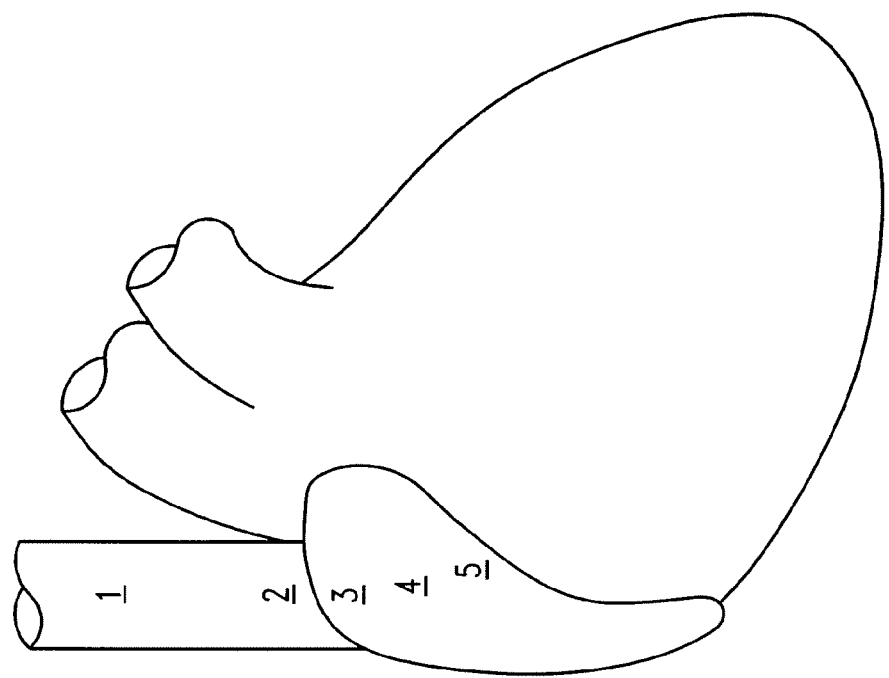

FIG. 2B is a series of exemplary P wave traces 1, 2, 3, 4, and 5 obtained from an electrode placed in each of the exemplary tip locations 1, 2, 3, 4, and 5 depicted in FIG. 2A, respectively.

Figure 3:
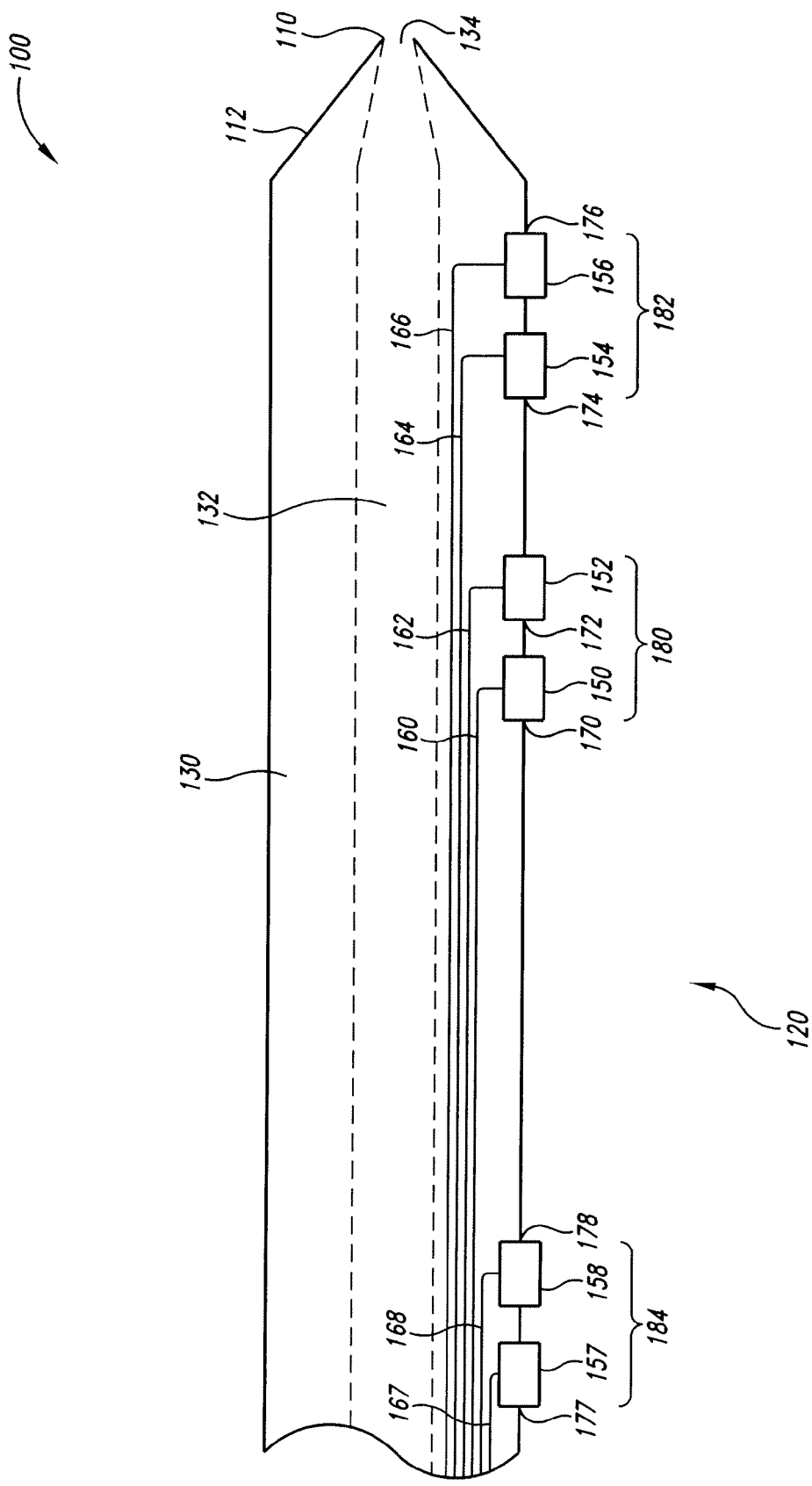

FIG. 3 is a CVC constructed in accordance with aspects of the present invention.

Figure 4:
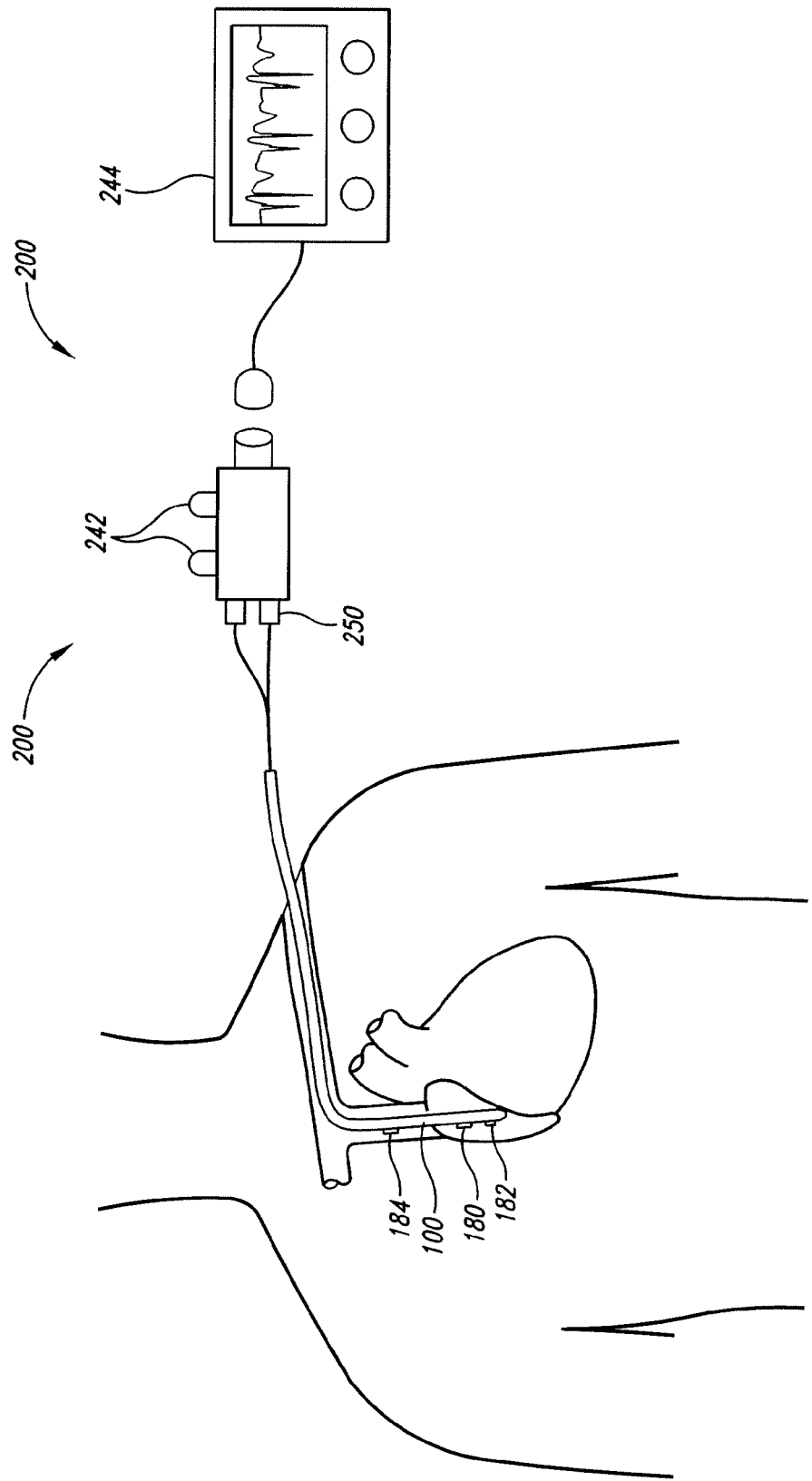

FIG. 4 is an embodiment of a signal analysis system for use with the CVC of FIG. 3.

Figure 5:
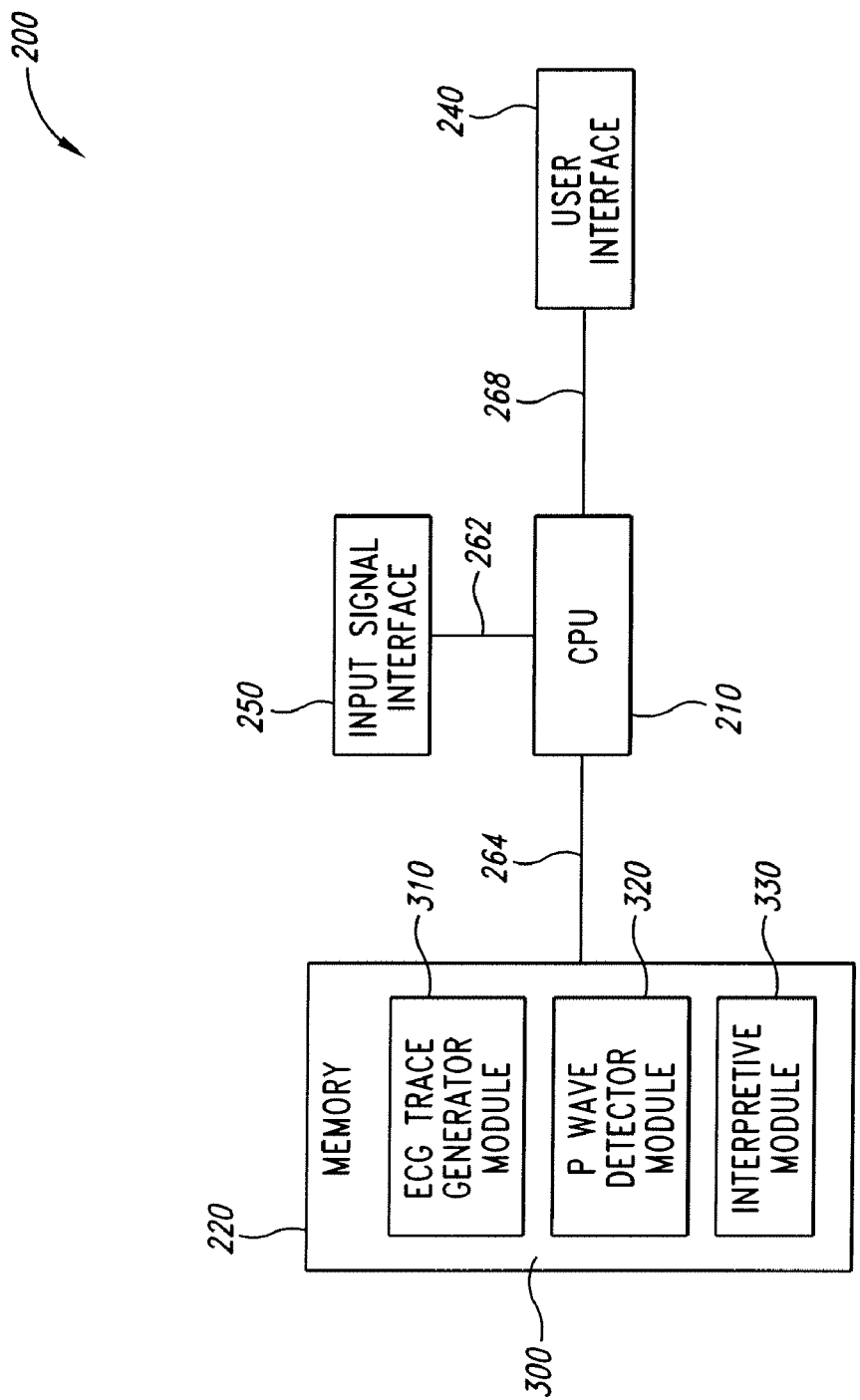

FIG. 5 is a block diagram illustrating the components of the signal analysis system of FIG. 4.

DETAILED DESCRIPTION OF THE INVENTION

Aspects of the present invention are directed toward a device for locating the tip of a CVC and a method of determining the location of the tip of a CVC. In the embodiment depicted in FIG. 3, the invention includes a CVC 100 constructed using any manner known in the art from a flexible nonconductive material, such as polyurethane or other suitable polymer material. It may also be desirable to use a radiopaque material. As is appreciated by those of ordinary skill in the art, the material used to construct the CVC 100 may include materials and/or coatings that provide improved anti-thrombotic or anti-bacterial properties. The CVC 100 has a body 130 configured to be received within a central vein. The body 130 may include a distal end 110 having a tapered tip 112 and a proximal end 120 spaced longitudinally along the body 130 from the distal end 110.

The body 130 may include one or more lumens 132 that traverse the length of the body and may have one or more openings 134 at or spaced from the tip 112. The openings 134 permit passage of material(s) between the lumen 132 and the environment outside the CVC 100. The lumens 132 may be used as conduits for the passage of materials such as medications and/or other fluids to and from the environment outside the CVC 100. For example, the lumen 132 may be used to aspirate blood into the CVC 100 and/or provide a conduit through which pressure data may be collected and used to construct pressure waveforms. The environment outside the CVC 100 may include the inside of the SVC, right atrium, and/or right ventricle. The CVC 100 is provided for illustrative purposes and those of ordinary skill in the art appreciate that alternate embodiments of CVC 100 including embodiments with additional lumens, a flow directed balloon tip, thermistors, thermodilution ports, pacing wire ports, embedded pacing electrodes, and the like are within the scope of the present invention.

In one embodiment, the invention includes four longitudinally spaced apart electrodes 150, 152, 154, and 156. Each electrode 150,152, 154, and 156 is in electrical communication with a wire 160, 162, 164, and 166, respectively. In one embodiment, the electrodes 150, 152, 154, and 156 are constructed from the distal end of each of the wires 160,162,164, and 166. In another embodiment, the electrodes 150, 152, 154, and 156 are attached to the ends of the wires 160, 162, 164, and 166 by any method known in the art for attaching an electrode to a wire, including soldering. The wires 160, 162, 164, and 166 are electrically isolated from one another. The wires 160, 162, 164, and 166 may be insulated from the environment outside the body 130 by the body 130.

The electrodes 150, 152, 154, and 156 and the wires 160, 162, 164, and 166 may be constructed from any suitable materials known in the art such as stainless steel or platinum. The electrodes 150, 152,154, and 156 may be about 6 mm to about 12 mm long, about 6 mm to about 12 mm wide, and about 1 mm to about 4 mm thick. The wires 160, 162,164, and 166 may be constructed using any electrical lead wire suitable for obtaining an ECG trace.

Optionally, the invention may include two longitudinally spaced apart electrodes 157 and 158. Each of the electrodes 157 and 158 may be electrical communication with a wire 167 and 168, respectively. The electrodes 157 and 158 and wires 167 and 168 may be constructed in a manner substantially similar to that used to construct the electrodes 150, 152, 154, and 156 and the wires 160, 162, 164, and 166, respectively. In one embodiment, the electrode 157 and 158 are positioned proximal to the electrodes 150, 152, 154, and 156.

Electrodes 150, 152, 154, and 156 may form two anode/cathode pairs. For example, electrodes 150 and 152 may form a first or proximal anode/cathode pair 180 and electrodes 154 and 156 may form a second or distal anode/cathode pair 182. Optional electrodes 157 and 158 may form an optional third or reference anode/cathode pair 184. A pair of electrodes forming an anode/cathode pair may be attached to a pair of insulated wires housed within a single cable. In one embodiment, a pair of bipolar lead wires are used. In this manner, the four electrodes of the proximal and distal anode/cathode pairs 180 and 182 may be attached to two lead wires. A third bipolar lead wire may be included for use with the reference anode/cathode pair 184. Alternatively, the proximal and distal anode/cathode pairs 180 and 182 may be attached to four insulated wires housed within a single cable such a dual bipolar lead wire.

The wires 160, 162, 164, and 166 and electrodes 150, 152, 154, and 156 may be permanently embedded into the body 130 of the CVC 100 or removably inserted into one or more channels or lumens 132 formed in the CVC 100 for potential future removal and/or replacement. The wires 167 and 168 and electrodes 157 and 158 may be incorporated into the CVC 100 in any manner described with respect to wires 160, 162, 164, and 166 and electrodes 150, 152, 154, and 156, respectively.

The electrodes 150, 152, 154, and 156 are in electrical communication with the environment outside the CVC 100. In one embodiment, a portion of each of the electrodes 150, 152, 154, and 156 are exposed to the environment outside the CVC 100 by apertures 170, 172, 174, and 176 formed in the body 130 adjacent to the electrodes 150, 152, 154, and 156, respectively. In embodiments including optional electrodes 157 and 158, a portion of each of the electrodes 157 and 158 may be exposed to the environment outside the CVC 100 by apertures 177 and 178 formed in the body 130 adjacent to the electrodes 157 and 158, respectively. The apertures 177 and 178 may be constructed in any manner suitable for constructing apertures 170, 172, 174, and 176. The apertures 170, 172, 174, and 176 may be formed in the body 130 by any method known in the art and the invention is not limited by the method used to construct the apertures 170, 172, 174, and 176. While the electrodes 150, 152, 154, and 156 depicted in the drawings extend outwardly from the body 130 through the apertures 170, 172, 174, and 176, it is understood by those of ordinary skill in the art, that electrodes 150, 152, 154, and 156 may reside at the bottom of the apertures 170, 172, 174, and 176 which may provide a passageway for fluids in the outside environment to the electrodes 150, 152, 154, and 156. Alternatively, the portion of the electrodes 150, 152, 154, and 156 in electrical communication with the environment outside the CVC 100 may be flush with the outside surface of the CVC 100.

The electrode 156 may be located at or spaced from the tip 112. In one embodiment, the electrode 156 is less than about 5 mm from the tip 112. The spacing between an anode and cathode of the anode/cathode pairs 180 and 182 may be about 1 mm to about 4 mm. In one embodiment, the spacing between an anode and cathode of the anode/cathode pairs 180 and 182 is about 3 mm.

In one embodiment, the distance between the electrodes 154 and 152 is less than the height of the right atrium. In an adult, the height of the right atrium may be approximately equal to or greater than about 4 cm. In one exemplary embodiment, the distance between the electrode 154 and 152 may be about 3 cm. In embodiments including optional electrodes 157 and 158, the distance between the electrodes 150 and 158 may be about 10 cm to about 18 cm.

Those of ordinary skill in the art appreciate that the size and spacing of the electrodes provided herein may require modification for use with patients that are larger or smaller than a typical adult and such embodiments are within the scope of the present invention. For example, smaller electrodes with a closer spacing may be required for use with a pediatric patient.

Referring to FIG. 4, the CVC 100 may gain venous access to the SVC by any method known in the art including inserting the CVC 100 in a standard sterile fashion through the subclavian, one of the jugular veins, or a peripheral vein and directing the tip 112 of the CVC 100 through that vein to the SVC.

Each of the anode/cathode pairs 180 and 182 may be used to generate an ECG trace. In this manner, the ECG waveforms detected by the proximal pair 180 may be compared to the ECG waveform detected by the distal pair 182. In one embodiment, the P wave portion of each trace is compared to determine the position of the tip 112 of the CVC 100 within the SVC, right atrium, and right ventricle.

In embodiments including the reference anode/cathode pair 184, the reference anode/cathode pair 184 may be used to generate an ECG trace. Referring to FIG. 4, because the reference anode/cathode pairs 184 may be located substantially proximally from the proximal and distal anode/cathode pairs 180 and 182, the reference anode/cathode pair 184 may remain in the SVC after the proximal and distal anode/cathode pairs 180 and 182 have entered the heart. In one embodiment, the spacing between the anode/cathode pair 184 and the proximal pair 180 is large enough to insure the reference anode/cathode pair 184 remains inside the SVC when the distal anode/cathode pair 182 is inside the right ventricle. In this manner, the reference anode/cathode pair 184, may be used to detect the ECG waveform within the SVC while the catheter is being placed.

The ECG waveforms detected by the proximal anode/cathode pair 180 and/or distal anode/cathode pair 182 may be compared to the ECG waveform detected by the reference anode/cathode pair 184. In one embodiment, the P wave portion of the ECG trace detected by the proximal anode/cathode pair 180 and/or distal anode/cathode pair 182 is compared to P wave portion of the ECG trace detected by the reference anode/cathode pair 184 to determine whether the tip 112 of the CVC 100 is located within the SVC, right atrium, or right ventricle.

The deflection of the trace, i.e., its vertical height relative to the baseline may be used to compare the P waves of the proximal and distal anode/cathode pairs 180 and 182. The deflection of the trace may also be used to compare the P waves of the proximal anode/cathode pair 180 and/or distal anode/cathode pair 182 to the reference anode/cathode pair 184. Because a P wave constitutes a voltage change over time, the deflection of the P wave is not constant. In one embodiment, the P wave is represented by an array or series of discrete numerical values.

The deflection value may be calculated in several ways. For example, the maximum or peak deflection may be used. Alternatively, the deflection value may be calculated as the difference between the maximum deflection and the minimum deflection. The deflection value may also be calculated as the sum of the absolute value of the maximum and minimum deflections. If the P wave has two peaks, which may occur when one of the anode/cathode pairs 180 and 182 are located within the right atrium (see position 4 of FIGS. 2A and 2B), the deflection value may be calculated by totaling the absolute value of the two peaks. When this method is used, the deflection value of the P wave measured at positions 3-5 may all be approximately equal. Further, if discrete data is being used, the discrete deflection quantities may be totaled. If continuous data is being used, the integral under the P wave may be used. Further, the average P wave deflection may be used. Because the polarity of portions of the P wave change depending upon the location of the anode/cathode pairs 180 and 182, it may be beneficial to use the absolute value of the deflection of the P wave to calculate the deflection value.

For the purposes of this application, the term "deflection value" will be used hereafter to describe the metric used to compare the P waves detected by the proximal and distal anode/cathode pairs 180 and 182. The deflection value may also be used to compare the P wave detected by the reference anode/cathode pair 184 to the P wave detected by one or both of the proximal and distal anode/cathode pairs 180 and 182. It is appreciated by those of ordinary skill in the art that the deflection value may be determined in numerous ways including those listed above and others not listed and the invention is not limited by the method and manner of determining the deflection value of the P wave.

In one exemplary embodiment, the deflection value is calculated as the sum of the absolute value of the maximum and minimum deflections when the maximum and minimum deflections have opposite polarities. The deflection value is calculated as the larger of the absolute value of the maximum and minimum deflections when the maximum and minimum deflections have the same polarity. In other words, the vertical height of the P wave is used. A first ratio of the deflection value of the distal anode/cathode pair 182 to the deflection value of the proximal anode/cathode pair 180 may be calculated.

When both of the anode/cathode pairs 180 and 182 are within the SVC, the deflection value of the P wave detected by each of them is substantially identical and the first ratio of their P wave deflection values equals approximately one. The deflection value of one or both of the P waves may be stored or otherwise recorded.

The user or operator may wish to continue advancing the CVC until the sino-atrial node is detected. When an anode/cathode pair 180 or 182 is approximately 1 cm to approximately 2 cm proximal to the sino-atrial node and therefore, by inference, approximately 1 cm to approximately 2 cm proximal to the entrance of the right atrium, the deflection value of the P wave detected by that anode/cathode pair may increase.

When the distal anode/cathode pair 182 enters the right atrium and the proximal anode/cathode pair 180 is still in the SVC, the deflection value of the P wave detected by the distal anode/cathode pair 182 may be at least double the deflection value of the P wave detected by the proximal anode/cathode pair 180. Therefore, the first ratio of the P wave deflection values of the distal anode/cathode pair 182 to the proximal anode/cathode pair 180 is greater than or equal to two. When this happens, the user or operator should withdraw the CVC 100.

A predetermined maximum threshold value may be used to determine whether the user or operator should withdraw the CVC 100. If the first ratio exceeds the maximum threshold value, the CVC 100 should be withdrawn. In one embodiment, the maximum threshold value may be approximately two.

When the distal anode/cathode pair 182 enters the right ventricle, the proximal anode/cathode pair 180 may be in the right atrium. Because the deflection value of the P wave experienced in the right ventricle is approximately equal to the deflection value of the P wave experienced in the SVC, the first ratio of the P wave deflection values of the distal anode/cathode pair 182 to the proximal anode/cathode pair 180 is less than or equal to about one half. Therefore, when the ratio is less than about one half, the user or operator should withdraw the CVC 100.

A predetermined minimum threshold value may be used to determine whether the user or operator should withdraw the CVC 100. If the first ratio is less than the minimum threshold value, the CVC 100 should be withdrawn. In one embodiment, the minimum threshold value may be approximately one half.

The distal anode/cathode pair 182 and the proximal anode/cathode pair 180 may be in the right atrium at the same time. When this occurs, the deflection value of the P waves detected by each would be very similar if not identical making their first ratio approximately equal to one. Therefore, a second ratio may be calculated to determine the location of the tip 112 of the CVC 100. The second ratio may include the ratio of the deflection value of the P wave detected by the proximal anode/cathode pair 180 to the deflection value of the P wave detected in the SVC. In one embodiment, the second ratio may include the ratio of the deflection value of the P wave detected by the proximal anode/cathode pair 180 to the deflection value of the P wave detected by the reference anode/cathode pair 184. In embodiments that include a reference anode/cathode pair 184, the reference anode/cathode pair 184 may detect the P wave in the SVC. Because the proximal anode/cathode pair 180 is inside the right atrium the deflection value of its P wave is greater than or equal to twice the deflection value of the P wave observed in the SVC. When the second ratio is equal to or greater than two, the user or operator should withdraw the CVC 100. The predetermined maximum threshold value may be used to determine whether the user or operator should withdraw the CVC 100. If the second ratio exceeds the maximum threshold value, the CVC 100 should be withdrawn.

Alternatively, a third ratio may be calculated to determine the location of the tip 112 of the CVC 100. The third ratio may include the ratio of the deflection value of the P wave detected by the distal anode/cathode pair 182 to the deflection value of the P wave detected in the SVC. In one embodiment, the third ratio may include the ratio of the deflection value of the P wave detected by the distal anode/cathode pair 182 to the deflection value of the P wave detected by the reference anode/cathode pair 184. In embodiments that include a reference pair 184, the reference pair 184 may detect the P wave in the SVC. Because the distal anode/cathode pair 182 is inside the right atrium, the deflection value of its P wave is greater than or equal to twice the deflection value of the P wave observed in the SVC. When third ratio is equal to or greater than two, the user or operator should withdraw the CVC 100. Under these circumstances, the predetermined maximum threshold value may be used to determine whether the user or operator should withdraw the CVC 100, i.e., if the third ratio exceeds the maximum threshold value, the CVC 100 should be withdrawn.

Determining when to withdraw the CVC 100 is unaffected by wide anatomic variability between individual people because instead of using predetermined threshold deflection values, the first, second, and/or third ratio of the deflection values obtained from each individual is used.

The following table summarizes the relationship between the location of the tip 112 of the CVC 100 and the deflection values of the P waves detected by the proximal and distal anode/cathode pairs 180 and 182:

|  | Location of the distal anode/cathode pair 182 | | | |
|---|---|---|---|---|
|  | SVC | Right Atrium | Right Atrium | Right Ventricle |
|  | Location of the proximal anode/cathode pair 180 | | | |
|  | SVC | SVC | Right Atrium | Right Atrium |
| First Ratio: Ratio of the deflection value of the distal anode/cathode pair 182 to the deflection value of the proximal anode/cathode pair 180 | $\approx 1$ | $\geq 2$ | $\approx 1$ | $\leq 0.5$ |
| Second Ratio: Ratio of the deflection value of the P wave detected by the proximal anode/cathode pair 180 and the deflection value of the P wave detected in the SVC | $\approx 1$ | $\approx 1$ | $\geq 2$ | $\geq 2$ |

-continued

| | Location of the distal anode/cathode pair 182 | | | |
|---|---|---|---|---|
| | SVC | Right Atrium | Right Atrium | Right Ventricle |
| | Location of the proximal anode/cathode pair 180 | | | |
| | SVC | SVC | Right Atrium | Right Atrium |
| Third Ratio: Ratio of the deflection value of the P wave detected by the distal anode/cathode pair 182 and the deflection value of the P wave detected in the SVC | ≈1 | ≧2 | ≧2 | ≈1 |

Because the voltage across each of the anode/cathode pairs 180 and 182 may vary depending over time, the voltage across wires 164 and 166 and wires 160 and 162 may each constitute a time-varying signal that can be analyzed using standard signal processing methods well known in the art. In a typical patient, the maximum of voltage across the anode/cathode pairs 180 and 182 may range from about 0.2 mV to about 3 mV. The signal from each anode/cathode pairs 180 and 182 may be amplified and/or filtered to improve the signal quality. A distal signal may be detected by the distal anode/cathode pair 182 and a proximal signal may be detected by the proximal anode/cathode pair 180. Similarly, an optional reference signal may be detected by the reference anode/cathode pair 184.

A separate ECG trace may be constructed for distal and proximal signals. In some embodiments, an ECG trace may also be constructed for the reference signal. The P wave portion of one or more of these ECG traces may be identified and analyzed. For example, the ECG trace of the distal signal may be visualized by connecting wires 164 and 166 of the distal anode/cathode pair 182 to a device such as a PACERVIEW® signal conditioner designed specifically to construct and display an ECG trace from a time varying low voltage signal. Similarly, the ECG trace of the proximal signal may be viewed by connecting the wires 160 and 162 of the proximal anode/cathode pair 180 to a PACERVIEW® signal conditioner. The ECG trace of the reference signal may be viewed by connecting the wires 167 and 168 of the proximal anode/cathode pair 184 to a PACERVIEW® signal conditioner.

In one embodiment, each of the four wires 160, 162, 164, and 166 may be coupled to a signal analysis system for analysis of the voltage information detected by the electrodes 150, 152, 154, and 156, respectively. In embodiments including electrodes 157 and 158, the wires 167 and 168 may be coupled to the signal analysis system for analysis of the voltage information detected by the electrodes 157 and 158, respectively. An exemplary signal analysis system 200 for analyzing the signals carried by wires 160, 162, 164, and 166 and alerting the user or operator when to withdraw the tip 112 of the CVC 100 may be viewed in FIG. 4. In an alternate embodiment, the system 200 may also analyze the signals carried by wires 167 and 168.

FIG. 5 is a block diagram of the components of the exemplary system 200. The system 200 may include a programmable central processing unit (CPU) 210 which may be implemented by any known technology, such as a microprocessor, microcontroller, application-specific integrated circuit (ASIC), digital signal processor (DSP), or the like. The CPU 200 may be integrated into an electrical circuit, such as a conventional circuit board, that supplies power to the CPU 210. The CPU 210 may include internal memory or memory 220 may be coupled thereto. The memory 220 may be coupled to the CPU 210 by an internal bus 264.

The memory 220 may comprise random access memory (RAM) and read-only memory (ROM). The memory 220 contains instructions and data that control the operation of the CPU 210. The memory 220 may also include a basic input/output system (BIOS), which contains the basic routines that help transfer information between elements within the system 200. The present invention is not limited by the specific hardware component(s) used to implement the CPU 210 or memory 220 components of the system 200.

Optionally, the memory 220 may include external or removable memory devices such as floppy disk drives and optical storage devices (e.g., CD-ROM, R/W CD-ROM, DVD, and the like). The system 200 may also include one or more I/O interfaces (not shown) such as a serial interface (e.g., RS-232, RS-432, and the like), an IEEE-488 interface, a universal serial bus (USB) interface, a parallel interface, and the like, for the communication with removable memory devices such as flash memory drives, external floppy disk drives, and the like.

The system 200 may also include a user interface 240 such as a standard computer monitor, LCD, colored lights 242 (see FIG. 4), PACERVIEW® signal conditioner, ECG trace display device 244 (see FIG. 4), or other visual display including a bedside display. In one embodiment, a monitor or handheld LCD display may provide an image of a heart and a visual representation of the estimated location of the tip 112 of the CVC 100. The user interface 240 may also include an audio system capable of playing an audible signal. In one embodiment, the user interface 240 includes a red light indicating the CVC 100 should be withdrawn and a green light indicating the CVC 100 may be advanced. In another embodiment, the user interface 240 includes an ECG trace display device 244 capable of displaying the ECG trace of the distal and proximal signals. In the embodiment depicted in FIG. 4, the user interface 240 includes a pair of lights 242, one red and the other green, connected in series with a ECG trace display device 244. In some embodiments, a display driver may provide an interface between the CPU 210 and the user interface 240.

The user interface 240 may permit the user to enter control commands into the system 200. For example, the user may command the system 200 to store information such as the deflection value of the P wave inside the SVC. The user may also use the user interface 240 to identify which portion of the ECG trace corresponds to the P wave. The user interface 240 may also allow the user or operator to enter patient information and/or annotate the data displayed by user interface 240 and/or stored in memory 220 by the CPU 210. The user interface 240 may include a standard keyboard, mouse, track ball, buttons, touch sensitive screen, wireless user input device and the like. The user interface 240 may be coupled to the CPU 210 by an internal bus 268.

Optionally, the system 200 may also include an antenna or other signal receiving device (not shown) such as an optical sensor for receiving a command signal such as a radio frequency (RF) or optical signal from a wireless user interface device such as a remote control. The system 200 may also include software components for interpreting the command signal and executing control commands included in the command signal. These software components may be stored in memory 220.

The system 200 includes an input signal interface 250 for receiving the distal and proximal signals. The input signal interface 250 may also be configured to receive the reference signal. The input signal interface 250 may include any standard electrical interface known in the art for connecting a double dipole lead wire to a conventional circuit board as well as any components capable of communicating a low voltage time varying signal from a pair of wires through an internal bus 262 to the CPU 210. The input signal interface 250 may include hardware components such as memory as well as standard signal processing components such as an analog to digital converter, amplifiers, filters, and the like.

The various components of the system 200 may be coupled together by the internal buses 262, 264, and 268. Each of the internal buses 262, 264, and 268 may be constructed using a data bus, control bus, power bus, I/O bus, and the like.

The system 200 may include instructions 300 executable by the CPU 210 for processing and/or analyzing the distal and/or proximal signals. These instructions may include computer readable software components or modules stored in the memory 220. The instructions 300 may include an ECG Trace Generator Module 310 that generates a traditional ECG trace from the distal and/or proximal signals. In some embodiments, the ECG Trace Generator Module 310 may generate a traditional ECG trace from the reference signal. As is appreciated by those of ordinary skill in the art, generating an ECG trace from an analog signal, such as the distal and proximal signals, may require digital or analog hardware components, such as an analog to digital converter, amplifiers, filters, and the like and such embodiments are within the scope of the present invention. In one embodiment, some or all of these components may be included in the input signal interface 250. In an alternate embodiment, some or all of these components may be implemented by software instructions included in the ECG Trace Generator Module 310. The ECG Trace Generator 310 may include any method known in the art for generating an ECG trace from a time varying voltage signal.

The instructions 300 may include a P Wave Detection Module 320 for detecting or identifying the P wave portion of the ECG trace. The P wave portion of the ECG trace may be detected using any method known in the art. In one embodiment, the P Wave Detection Module 320 receives input from the user or operator via the user interface 240. The input received may identify the P wave portion of the ECG trace.

The instructions 300 may include an Interpretive Module 330 for comparing the P wave generated for the distal, proximal, and/or reference signals. In one embodiment, the Interpretive Module 330 determines the deflection value of the P wave generated for the distal and/or proximal signals. In some embodiments, the Interpretive Module 330 determines the deflection value of the P wave generated for the reference signal. The Interpretive Module 330 may direct the CPU 210 to store the deflection value of the distal, proximal, and/or reference signals in memory 220. In particular, it may be desirable to store the deflection value of the P wave encountered in the SVC. The Interpretive Module 330 may receive input from the user or operator via the user interface 240 instructing the Interpretive Module 330 to store the deflection value.

The Interpretive Module 330 may also determine the first ratio by calculating the ratio of the deflection value of the distal signal to the deflection value of the proximal signal. If the first ratio is approximately equal to or greater than the maximum threshold value, the tip 112 of the CVC 100 may be in the right atrium. The Interpretive Module 330 may alert the user or operator that the tip 112 is in the right atrium and the CVC 100 should be withdrawn from the right atrium. On the other hand, if the first ratio is approximately equal to or less than the minimum threshold value, the tip 112 of the CVC 100 may be in the right ventricle. The Interpretive Module 330 may alert the user or operator that the tip 112 is in the right ventricle and the CVC 100 should be withdrawn therefrom.

If the first ratio is less than the maximum threshold value and greater than the minimum threshold value, the tip 112 may be in either the right atrium or the SVC. When this happens, the Interpretive Module 330 may calculate either the second ratio or third ratio. If the second or third ratio is approximately equal to or greater than the maximum threshold value, the tip may be in the right atrium and should be withdrawn therefrom. The Interpretive Module 330 may alert the user or operator that the tip 112 is in the right atrium. If the second or third ratio is approximately less than the maximum threshold value, the tip 112 is in the SVC and may be advanced if the operator so chooses. The Interpretive Module 330 may communicate to the user or operator that the tip 112 may be advanced.

In an alternate embodiment, the second ratio may be calculated first. Whenever the second ratio is approximately equal to or greater than the maximum threshold value, the user or operator may be alerted to withdraw the CVC 100. If the second ratio is approximately less than the maximum threshold value, the first or third ratio may be calculated and used to determine the position of the tip 112 of the CVC 100.

In one embodiment, the instructions in the Interpretive Module 330 direct the CPU 210 to use the user interface 240 to communicate whether the tip 112 should be withdrawn to the user. The CPU 210 may use the user interface 240 to communicate the tip 112 may be advanced.

While exemplary minimum and maximum threshold values have been provided as a general guideline, those of ordinary skill in the art appreciate that these values may benefit from adjustment as additional anatomic or electrophysiologic data is acquired and such modified values are within the scope of the present invention. Because the Interpretive Module 330 may interpret the P wave to obtain the deflection values of the distal and proximal signals, compare the deflection values and provide the operator with immediate real-time feedback, the operator need not interpret the actual ECG waveforms.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A method of locating a tip of a central venous catheter, the central venous catheter having a portion disposed within the superior vena cava, a distal pair of electrodes, and a proximal pair of electrodes spaced longitudinally from the distal pair of electrodes, the method comprising:
   obtaining a distal electrical signal from the distal pair of electrodes;
   generating a first P wave from the distal electrical signal;
   determining a first deflection value of the first P wave;
   obtaining a proximal electrical signal from the proximal pair of electrodes;
   generating a second P wave from the proximal electrical signal;
   determining a second deflection value of the second P wave;
   calculating a first ratio from the first and second deflection values;
   obtaining a SVC deflection value;
   calculating a second ratio of one of the first and second deflection values to the SVC deflection value; and
   determining a location of the tip of the central venous catheter based on the first ratio and the second ratio.

2. The method of claim 1, wherein determining the location of the tip of the central venous catheter based on the first ratio and the second ratio comprises:
   comparing the first ratio to a maximum threshold value; and
   concluding the tip of the central venous catheter is located in the right atrium if the first ratio is equal to or exceeds the maximum threshold value.

3. The method of claim 1, wherein determining the location of the tip of the central venous catheter based on the first ratio and the second ratio comprises:
   comparing the first ratio to a minimum threshold value; and
   concluding the tip of the central venous catheter is located in the right ventricle if the first ratio is equal to or less than the minimum threshold value.

4. The method of claim 1, wherein determining the location of the tip of the central venous catheter based on the first ratio and the second ratio comprises:
   comparing the first ratio to a maximum threshold value and a minimum threshold value; and
   concluding the tip may be located in either the superior vena cava or the right atrium if the first ratio is less than the maximum threshold value and greater than the minimum threshold value.

5. The method of claim 1, wherein the portion of the central venous catheter disposed within the superior vena cava has a reference pair of electrodes spaced longitudinally proximally from the proximal pair of electrodes, and obtaining the SVC deflection value comprises:
   obtaining a reference electrical signal from the reference pair of electrodes;
   generating a SVC P wave from the reference signal; and
   determining the SVC deflection value from the SVC P wave.

6. The method of claim 5, wherein determining the location of the tip of the central venous catheter based on the first ratio and the second ratio comprises:
   comparing the second ratio to a maximum threshold value; and
   concluding the tip of the central venous catheter is located in the right atrium or right ventricle when the second ratio is equal to or exceeds the maximum threshold value.

7. The method of claim 1, wherein determining the SVC deflection value comprises:
   positioning the distal pair of electrodes inside the superior vena cava;
   obtaining a SVC electrical signal from the distal pair of electrodes;
   generating a SVC P wave from the SVC signal; and
   calculating the SVC deflection value from the SVC P wave.

8. The method of claim 1, wherein determining the SVC deflection value comprises:
   positioning the proximal pair of electrodes inside the superior vena cava;
   obtaining a SVC electrical signal from the proximal pair of electrodes;
   generating a SVC P wave from the SVC signal; and
   calculating the SVC deflection value from the SVC P wave.

9. The method of claim 1, wherein the first P wave comprises a maximum value and a minimum value;
   calculating the first deflection value as a function of the first P wave comprises determining the larger of the absolute value of the maximum value and the absolute value of the minimum value when the maximum and minimum values have the same polarity; and
calculating the first deflection value as a function of the first P wave comprises totaling the absolute values of the maximum and minimum values when the maximum and minimum values have opposite polarities.

* * * * *